United States Patent [19]

Sharpless et al.

[11] Patent Number: 5,162,554
[45] Date of Patent: Nov. 10, 1992

[54] OPTICALLY ACTIVE ENANTIOMERS OF SUBSTITUTED GLYCERALDEHYDES OR GLYCIDALDEHYDES FORMED AS SUBTITUTED 1,5-DIHYDRO-3H-2,4-BENZODIOXEPINES

[75] Inventors: K. Barry Sharpless, La Jolla; Ryu Oi, San Diego, both of Calif.

[73] Assignee: Massachusetts Institute of Technology, Cambridge, Mass.

[21] Appl. No.: 716,902

[22] Filed: Jun. 18, 1991

[51] Int. Cl.$^5$ .................................. C07D 411/04
[52] U.S. Cl. .................................. 549/34; 549/214; 549/229; 549/230; 549/350
[58] Field of Search ............... 549/34, 229, 230, 350, 549/214

[56] References Cited

PUBLICATIONS

Hertel et al., *Synthetic Comm.* 21(2) 151–154 (1991).
N. Machinaga et al., *Tet. Letters*, "1,5–Dihydro–3H–2,4 benzodioxepine as a novel carbonyl protecting group," 30(31) pp. 4165–4168 (1989).
H. Patney, *Tet. Letters*, "Sulfonated charcoal, a mild and efficient reagent for the preparation of cyclic acetals . . . " 32(3) pp. 413–416 (1991).
K. Sharpless, et al., *J. Org. Chem.*, "Rapid Separation of organic mixtures by formation of metal complexes," 40(9), pp. 1252–1257 (1975).
J. Jurezak et al., *Tetrahedron*, "(R)–and (S)–2,3–O–isopropylideneglyceraldehyde in stereoselective organic synthesis," 42(2) pp. 442–488 (1986).

Primary Examiner—Richard L. Raymond
Assistant Examiner—Mark W. Russell
Attorney, Agent, or Firm—Hamilton, Brook, Smith & Reynolds

[57] ABSTRACT

Stable, optically active enantiomers of substituted glyceraldehydes or glycidaldehydes are synthesized by using osmium-catalyzed asymmetric dihydroxylation of an olefin which is a substituted 1,5-dihydro-3H-2,4-benzodioxepine. For example, the protected glyceraldehyde, 3-(1,2-dihydroxyethyl)-1,5-dihydro-3H-2,4-benzodioxepine and the protected glycidaldehyde, 3-(1,2-epoxyethyl)-1,5-dihydro-3H-2,4-benzodioxepine have been synthesized and the optical enantiomer has been recovered. In the synthetic and isolation methods, enantiomers with high enantiomeric excess are recovered from the mother liquor following a recrystallization step.

8 Claims, No Drawings

OPTICALLY ACTIVE ENANTIOMERS OF SUBSTITUTED GLYCERALDEHYDES OR GLYCIDALDEHYDES FORMED AS SUBTITUTED 1,5- DIHYDRO-3H-2,4-BENZODIOXEPINES

GOVERNMENT SUPPORT

Work described herein was supported by Grant No. GM 28384 from the National Institutes of Health and the the U.S. Government may have rights pertaining to this invention as a result of this grant.

BACKGROUND OF THE INVENTION

Contemporary asymmetric synthesis is a widely used method for stereocontrolled creation of stereogenic centers in organic molecules. During recent years, this approach to organic synthesis greatly contributed to progress in the directed introduction of various functionalities and in the highly controlled formation of new centers of chirality. These processes still remain the basic problems in the total synthesis of natural products or medicinals. Preparation of the latter in optically pure form by application of chiral starting materials is very advantageous, enabling precise planning and efficient realization of synthetic pathways.

Many monosaccharides and their readily available derivatives are versatile substrates for the synthesis of optically active target molecules. For example, 2,3,0-isopropylideneglyceraldehyde (1) has been widely used as one of the chosen substrates; it is characterized by availability of both enantiomers from natural sources, and by pronounced versatility due to the presence of the aldehyde and protected diol functionality in the same small molecule.

Another building block for various bioactive compounds is glycidaldehyde (2).

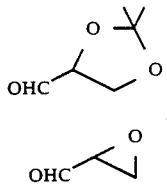

Although compounds (1) and (2) have enjoyed considerable success as substrates in synthesis routes to other substances, they suffer from some severe disadvantages. Despite the versatility of optically active glycidaldehyde (2), its high volatility and high genotoxicity, in addition to its high solubility in aqueous solutions, have restricted its wide use. Additionally, both chiral building blocks (1) and (2) are unstable and no commercial supply of these compounds exists so far.

It is readily apparent that there is a need for compounds like (1) and (2) which can be stored for extended periods of time and are not hazardous.

SUMMARY OF THE INVENTION

This invention pertains to optically active enantiomers of substituted glyceraldehydes or glycidaldehydes formed as substituted 1,5-dihydro-3H-2,4-benzodioxepines and methods of preparation of these enantiomers. The general formulae for these enantiomers are as follows:

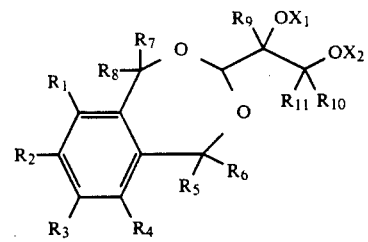

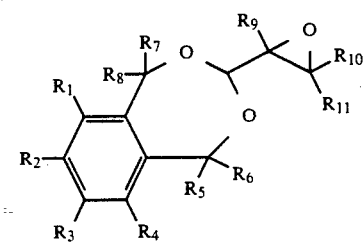

A variety of substituents can exist at positions designated $R_1-R_{11}$ and $X_1-X_2$. The substituents at positions $R_1-R_4$ independently can be H, alkyl, aryl, hydroxy, alkoxy, aryloxy, halo, nitro, amino or cyano groups. The substituents at positions $R_5-R_{11}$ independently can be H, alkyl or aryl groups. At positions $X_1$ or $X_2$, the substituents independently can be H, alkyl, aryl, alkylcarbonyl, alkylsulfonyl, arylcarbonyl, arylsulfonyl or silyl groups. In some instances, $X_1$ and $X_2$ are chosen such that a cyclic structure is formed that includes the oxygens to which $X_1$ and $X_2$ are bonded. In preferred embodiments, the cyclic structure is a 5-membered ring and the atom that bridges the two oxygens is either carbon or sulfur.

Particularly preferred embodiments of the invention are the protected glyceraldehyde, 3-(1,2-dihydroxyethyl)-1,5-dihydro-3H-2,4-benzodioxepine (3) and the protected glycidaldehyde, 3-(1,2-epoxyethyl)-1,5-dihydro-3H-2,4-benzodioxepine (4).

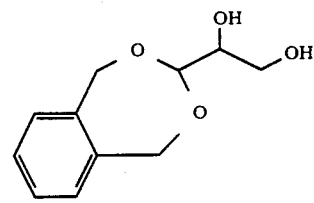

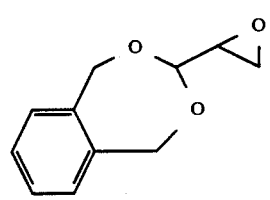

The protected glyceraldehyde, 3-(1,2-dihydroxyethyl)-1,5-dihydro-3H-2,4-benzodioxepine (3) and protected glycidaldehyde, 3-(1,2-epoxyethyl)-1,5-dihydro-3H-2,4-benzodioxepine (4) are stable substitutes for (1) and (2). Both of these protected aldehydes are solid at ambient temperature and are easily handled. Enantiopure (3) and (4) can be stored for a long time without special care and are readily transformed to essential chiral derivatives. The merits of (3) and (4) include the potential that nucleophilic modifications can be performed prior to the modifications of the nascent aldehyde functionality. Furthermore, deprotection of the acetal to the corresponding aldehyde is easily performed by catalytic hydrogenation under neutral conditions. For example, transformation of (3) to (1) is easily performed by the acetonization followed by catalytic hydrogenation.

Another embodiment of this invention is an olefin with the formula:

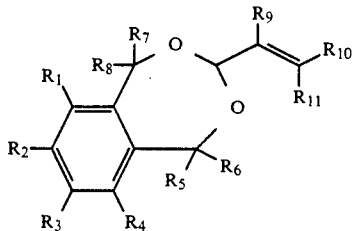

where $R_1$–$R_{11}$ independently can be the substituents as previously listed for these radical designations.

This invention also pertains to methods of producing the optically active enantiomers. In these methods, an acrolein is reacted with 1,2-benzenedimethanol to form a vinyl-2,4-benzodioxepine which, in turn, is asymmetrically dihydroxylated by an osmium. catalyzed reaction to form a diol. An initial recrystallization of the diol is performed and a higher enantiomeric excess of optical enantiomer is recovered from the remaining mother liquor.

In a preferred embodiment of the method, the olefin, vinyl-2,4-benzodioxepine, is slowly added to a concentrated solution of the reactants needed to perform the osmium-catalyzed asymmetric dihydroxylation reaction. The initial recrystallization and recovery steps are then performed. With this embodiment, a higher enantiomeric excess of the optical enantiomer is achieved than without the slow addition of a the olefin to the concentrated solution of osmium-catalyzed asymmetric dihydroxylation reactants.

In another preferred embodiment of the method, the recovery of the optical enantiomer is accomplished by adding a metal halide, such as $MgCl_2$, and a trace amount of a small hydroxyl-bearing molecule to the mother liquor from the recrystallization step. A precipitable complex is formed between the metal halide and the optical enantiomer. This precipitate is dissolved in a mixture of water and phase-separable organic solvent, the phase-separable organic solvent is separated from the water and the optical enantiomer is recovered from the separated phase-separable organic solvent.

DETAILED DESCRIPTION OF THE INVENTION

This invention pertains to substituted glyceraldehydes or glycidaldehydes formed as substituted 1,5-dihydro-3H-2,4-benzodioxepines and methods of preparing these compositions. In particular, optically active enantiomers of the substituted 1,5-dihydro-3H-2,4-benzodioxepines are included in the invention.

The general formulae for the optically active enantiomers is shown in the Summary of the Invention section. These general formulae are based on organic structures shown by (3) and (4). A variety of substituents at various positions of these structures are included in this invention. These substituents include, for example, H, alkyl, aryl, hydroxy, alkoxy, aryloxy, halo, nitro, amino or cyano groups at positions $R_1$ through $R_4$; H, alkyl or aryl groups at positions $R_5$ through $R_{11}$; and H, alkyl, aryl, alkylcarbonyl, alkylsulfonyl, arylcarbonyl, arysulfonyl or silyl groups at positions $X_1$ or $X_2$. The substituents can be the same at one or more of the designated substituent positions or they can differ from each other. That is, the identity of the substituent at each designated position is independent of the identity of the substituents at the remaining positions.

In a preferred embodiment of the invention, $X_1$ and $X_2$ are substituents that are chosen to close the system including the oxygen atoms, to which $X_1$ and $X_2$ are bonded, into a cyclic or ring structure. In particularly preferred embodiments of the invention, the cyclic closure forms a 5-membered ring. The bridging atom between the two oxygens can be sulfur. More preferably, the bridging atom is carbon, thereby forming a 1,3-dioxolane structure. When sulfur is the bridging atom in the 5-membered ring, it can be bonded to one additional oxygen (forming a sulfite) or to two additional oxygens (forming a sulfate). When carbon is the bridging atom in the 5-membered ring, it can be bonded to an additional oxygen, thereby forming a carbonyl structure or to two other substituents such as H, alkyl or aryl groups.

Particularly preferred embodiments of the invention occur when $R_1$ through $R_{11}$ and $X_1$ and $X_2$ are all H. These embodiments are structures (3) and (4) which are stable compounds that are particularly useful as starting materials for a variety of organic synthesis routes. These embodiments are also optically active enantiomers which confer characteristics upon them that are often required for particular synthesis objectives.

Another embodiment of the invention is the olefin 3-vinyl-1,5-dihydro-3H-2,4-benzodioxepine and substituted forms of the olefin. A variety of substituents can exist at various positions of this olefin. These substituents are designated $R_1$ through $R_{11}$ and the designated positions and compositions of these substituents are indentical with those of the general formulae shown in the Summary of the Invention section. Thus, for substituents $R_1$ through $R_4$, the radicals can include, for example, H, alkyl, aryl, hydroxy, alkoxy, aryloxy, halo, nitro amino or cyano groups and for substituents $R_5$ through $R_{11}$, the radicals can include, for example, H, alkyl or aryl groups. These olefins are preferred starting materials for the synthesis of the substituted 1,5-dihydro-3H-2,4-benzodioxepines of the general formulae shown in the Summary of the Invention section.

These olefins are not necessarily optically active compounds (i.e., their optical activity, if it exists, is due to the $R_5$ and $R_6$ or $R_7$ and $R_8$ substituents) but yield the optically active enantiomers of the invention.

The invention also includes methods of preparing optically active enantiomers such as the protected glyceraldehyde 3-(1,2-dihydroxyethyl)-1,5-dihydro-3H-2,4-benzodioxepine. In the first step of the method, an acrolein is reacted with a 1,2-benzenemethanol to give an olefin, 3-vinyl-1,5-dihydro-3H-2,4-benzodioxepine. This olefin product is then subjected to an osmium-catalyzed asymmetric dihydroxylation reaction. This reaction involves the use of an osmium-containing catalyst, such as potassium osmate (VI) dihydrate, an oxidant, such as potassium ferricyanide, and a chiral ligand, such as dihydroquinidine-9-0-(9'-phenanthryl)ether, to form an asymmetric dihydroxylation reaction at the two carbons of the olefin double bond. Under preferred conditions, this osmium-catalyzed asymmetric dihydroxylation reaction is carried out in a equivolume mixture of t-butyl alcohol and water at 0° C. with potassium carbonate present in the reaction solution.

The product of the osmium-catalyzed asymmetric dihydroxylation reaction is brought into an organic solvent (e.g., t-butyl alcohol plus methylene chloride extractions of the aqueous phase) where a crystallization of the product occurs. This product is then recrystallized from an organic solvent. The recrystallized solid material is separated from the mother liquor by a technique such as filtration and the final product is recovered from the mother liquor phase by a purification process such as column chromatography. These latter steps in the method of the invention are important because the enantiomeric excess of the product, given as %ee, is much greater for the material from the mother liquor than either the solid material separated by filtration or the originally crystallized product (e.g., respectively, 97%ee versus 53%ee versus 86%ee). Since the production of an optically active enantiomer is the sought outcome, these latter steps of the invention are needed to achieve this result.

In a particularly preferred embodiment of the method, the osmium-catalyzed asymmetric dihydroxylation reaction is performed by the slow addition of a solution of the olefin to a concentrated solution of the osmium-containing catalyst, the chiral ligand and the oxidant. This procedure yields more enantiomeric product with less asymmetric dihydroxylation reaction solvent. For example, the product concentration can be from about 20 g/l to about 100 g/l. With this procedure, the chemical yield as well as the enantiomeric excess of the product are great. Without slow addition of the olefin solution to the concentrated reactants, the enantiomeric excess of the product is much lower (e.g., 67%ee) than with slow addition (e.g., 84%ee). This is important, particularly, for industrial scale purposes.

In another particularly preferred embodiment of the method, the recrystallization step is followed by a metal halide complexation step and the final enantiomeric product is recovered from the metal halide complexes that were formed in this complexation step. The recrystallization step in this embodiment can be performed with a variety of non-alcohol organic solvents including aliphatic hydrocarbons (e.g., hexane or heptane), aromatic hydrocarbons (e.g., benzene, toluene, xylene), ethers (e.g., diethyl ether, DME), esters (e.g., ethyl acetate) and halogenated organic solvents (e.g., $CH_2Cl_2$, $CHCl_3$, $CCl_4$, $CH_2Br_2$). Following recrystallization, the recrystallized solid material is separated from the mother liquor. A metal halide, such as $CaCl_2$, $CaBr_2$, $MgCl_2$ $MnCl_2$ or $CoCl_2$, plus a trace amount (i.e. about 1%) of a small hydroxyl-bearing molecule are added to the mother liquor. The small hydroxyl-bearing molecule can be, for example, a small alcohol, such as methanol, ethanol, n-propanol, or t-butanol, or water, such as the water of hydration of the metal halide. In preferred embodiments, anhydrous $CaCl_2$ is used with a trace amount of a small n-alcohol. The metal halide and the diol from the osmium-catalyzed asymmetric dihydroxylation reaction interact to produce alcoholate complexes which form a precipitate in the mother liquor. This precipitate is separated from the mother liquor (e.g., by filtration) and dissolved in a mixture of water and phase-separable organic solvent (preferably methylene chloride). The optically active enantiomeric diol is liberated from the metal halide complex and dissolved in the organic phase. The organic phase is separated from the aqueous phase and the optically active enantiomer is recovered from this phase-separable organic solvent by an extration process. This procedure yields an optically active enantiomer with great purity.

The mother liquor, from which the metal halide-diol complexes are separated, contains the chiral ligand which is necessary for the osmium-catalyzed asymmetric dihydroxylation reaction of the invention. This chiral ligand which is not routinely available, can be recovered from this mother liquor phase by a recovery process such as column chromatography or recrystallization for future reuse.

The invention will be illustrated by the following examples which should not be construed as limiting the invention in any manner.

EXAMPLE 1

Synthesis of 3-(1,2-dihydroxyethyl)-1,5-dihydro-3H-2,4-benzodioxepine and 3-(1,2-epoxyethyl)-1,5-3H-2,4-benzodioxepine

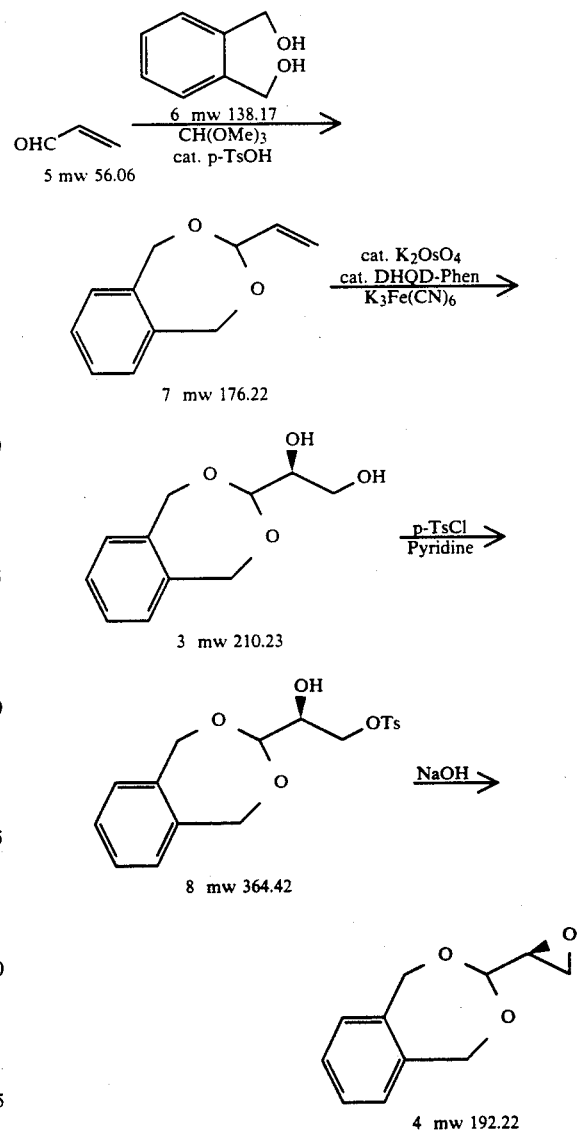

Reaction from (5) to (7)

3-Vinyl-1,5-dihydro-3H-2,4-benzodioxepine (7) was prepared from acrolein (5) and 1,2-benzenedimethanol (6) in the presence of a catalytic amount of p-toluenesulfonic acid according to a reported procedure (M. Machinaga, et al., *Tetrahedron Lett.*, 30:4165 (1989)). That is, a solution consisting of (5), (6), trimethyl orthoformate and a trace amount of p-toluenesulfonic acid in 1,2-dimethoxyethane was stirred at room temperature for 3h. The reaction mixture was diluted with ether, washed with a cold, saturated aqueous solution of NaHCO$_3$ and dried over MgSO$_4$. After evaporation of the solvent, the resulting product (7) was purified by column chromatography or distillation (b.p. 116°–118° C. (5mm Hg)) for subsequence use.

Reaction from (7) to (3)

To a well-stirred mixture of dihydroquinidine-9-0-(9'-phenanthryl)ether (0.10 g. 0.2 mmol. K. B. Sharpless et al., *J. Org. Chem.*, in press), potassium ferricyanide (9.88 g, 30.0 mmol), potassium carbonate (4.15 g, 30.0 mmol). and potassium osmate (VI) dihydrate (K$_2$OsO$_4$.2H$_2$O, 0.007g, 0.02 mmol) in a t-butyl alcohol-water mixture (150 mL, 1:1, v/v) at 0° C., 3-vinyl-1,5-dihydro-3H-2,4-benzodioxepine (7) (1.76 g, 10.0 mmol) was added. The reaction mixture was stirred for 24 h at 0° C. Solid sodium metabisulfite (Na$_2$S$_2$O$_5$, 5.70 g) was added and the mixture was stirred for an additional hour. Two phases were separated, and the water phase was extracted with methylene chloride (100 mL×3). The combined extracts (t-BuOH-phase and CH$_2$Cl$_2$-phase were dried (Na$_2$SO$_4$) and concentrated, giving pale yellow crystals (2.02 g, 96% crude yield from (7), 86%ee by Mosher's method). Recrystallization from hot benzene (150 mL) was performed, and the precipitated white solid was filtered ((3), 0.42 g, 20% yield from (7) 53%ee). The mother liquor was concentrated and the residue was purified by column chromatography (silica gel, hexane-ethyl acetate), giving a white solid (3-(1S,2-dihydroxyethyl)-1,5-dihydro-3H-2,4-benzodioxepine (3), 1.26 g, mp=73°–75° C., $[\alpha]^{23}_D = -12.4°$(c 2.62 CHCl$_3$) 60% yield form (7) 97%ee).

Reaction from (3) to (8)

To a solution of 3-(1S,2-dihydroxyethyl)-1,5-dihydro-3H-2,4-benzodioxepine (3) (97%ee, 1.00 g, 4.76 mmol) in pyridine (10 mL), p-toluene sulfonyl chloride (1.00 g, 5.25 mmol) was added at 0° C., and was stirred for 24 h at room temperature. The reaction mixture was poured into cold water (30 mL) and extracted with ether (30 mL×3). The combined organic extracts were washed with cold 10% aqueous hydrochloric acid (20 mL×3) and brine (5 mL×2). The organic phase was dried (Na$_2$SO$_4$) and concentrated. The residue was purified by column chromatography (silica gel. hexane-ethyl acetate), giving 3-(1S-hydroxy-2-(p-toluenesulfonyl)oxyethyl)-1,5-dihydro-3H -2,4-benzodioxepine (8) (1.47 g, 85% yield from (3)).

Reaction from (8) to (4)

The mixture of 3-(1S-hydroxy-2(p-toluenesulfonyl)oxyethyl-1,5-dihydro-3H- 2,4-benzodioxepine (8) (97%ee, 0.40 g, 1.16 mmol) and NaOH (1.10 mmol, prepared from 0.063 g NaOMe in 1 mL H$_2$O) in methyl alcohol (5 mL) were refluxed for 1 h. The reaction mixture was poured into a cold water (10 mL) and extracted with ether (10 mL×3). The combined organic extracts were dried (Na$_2$SO$_4$) and concentrated. The residue was purified by column chromatography (silica gel, hexane-ethyl acetate), giving white solid (3-(1S,2-epoxyethyl)-1,5-dihydro-3H-2,4-benzodioxepine (4) (0.19 g, 90% yield from (8), $[\alpha]^{23}_D = -1.0°$ (c 2.97 CHCl$_3$), 97%ee by chiral HPLC).

EXAMPLE 2

Alternative Synthesis and Recovery of 3-(1,2-dihydroxyethyl)-1,5-dihydro-3H-2,4-benzodioxepine; Reaction from (7) to (3), CaCl$_2$ Purification Method Reaction To a well-stirred mixture of dihydroquinidine-9-0-(9'-phenanthryl)ether (1.00 g 2.0 mmol, potassium ferricyanide (197.56 g. 600 mmol). potassium carbonate (82.93 g, 600 mmol), and potassium osmate (VI) dihydrate (K$_2$OsO$_4$2H$_2$O, 0.147g, 0.4 mmol) in a t-butyl alcohol-water mixture (700 mL, 1:1, v/v) at 0° C., 3-vinyl-1,5-dihydro-3H-2,4-benzodioxepine (7) (35.24 g, 200 mmol) was added dropwise over a period of 24 h. The reaction mixture was stirred for an additional 24 h. at 0° C. (total 48 h.) and was diluted with water (1000 mL). Sodium metabisulfite (Na$_2$S$_2$O$_5$, 114.06g. 600 mmol) was slowly added, and the mixture was stirred for 3 h. Two phases were separated, and the water phase was extracted with methylene chloride (200 mL×3). The combined extracts (t-BuOH-phase and CH$_2$Cl$_2$-phase) were dried (Na$_2$SO$_4$) and concentrated, giving pale yellow crystals (39.86g. 95% crude yield from (7) 84%ee by Mosher's method). Without slow addition, enantiomeric excess was 67%ee under the same reaction conditions.

Isolation and Purification

Recrystallization of crude mixture (39.86 g) from anhydrous hot ethyl acetate (800 mL) was performed, and the precipitated white solid was filtered ((3) 9.41 g, 22% yield from (7) 53%ee). Freshly powdered anhydrous calcium chloride (22.20 g, 200 mmol) and ethyl alcohol (0.055 g, 1.2 mmol) were added to the stirred mother liquor solution, and vigorous stirring was continued at room temperature for 10 h. The heterogeneous reaction mixture was filtered, and the resulting CaCl$_2$ complex of diol (3) was washed with hexane (20 mL×3). This complex was then added to a separatory funnel containing ice-cold water (200 mL) and methylene chloride (200 mL), and shaken vigorously until it dissolved. The CH$_2$Cl$_2$-phase was separated, and the aqueous phase was extracted with methylene chloride (200 mL×2.) The combined organic phase was washed with water (200 mL) and then dried (Na$_2$SO$_4$) and concentrated, giving a white solid (3-(1S,2-dihydroxyethyl)-1,5-dihydro-3H-2,4-benzodioxepine (3), 23.15 g 55% yield from (7). 97%ee). The mother liquor was concentrated and the chiral ligand, dihydroquinidine-9-0-(9'-phenanthryl)ether, was recovered (0.90 g, 90% recovery) by column chromatography (silica gel, ethyl acetate-methanol).

Equivalents

Those skilled in the art will recognize, or be able to ascertain, using no more than routine experimentation, many equivalents to the specific embodiments of the invention described herein. Such equivalents are intended to be encompassed in the scope of the following claims.

We claim:

1. A substituted 1.5-dihydro-3H-2,4-benzodioxepine of the formula:

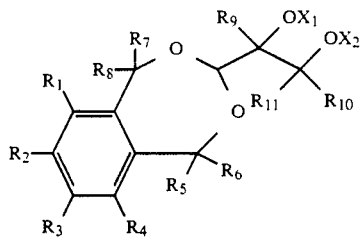

wherein
- $R_1$, $R_2$, $R_3$ or $R_4$ are independently chosen from the group consisting of H, alkyl, aryl, hydroxy, alkoxy, aryloxy, halo, nitro, amino and cyano;
- $R_5$, $R_6$, $R_7$, $R_8$, $R_9$, $R_{10}$ or $R_{11}$ are independently chosen from the group consisting of H, alkyl and aryl; and
- $X_1$ and $X_2$ are independently chosen from the group consisting of H, alkyl, aryl, alkylcarbonyl, alkylsulfonyl, arylcarbonyl, arylsulfonyl and silyl.

2. The composition of claim 1 wherein $R_1$, $R_2$, $R_3$, $R_4$, $R_5$, $R_6$, $R_7$, $R_8$, $R_9$, $R_{10}$, $R_{11}$, $X_1$ and $X_2$ are H.

3. A substituted 1,5-dihydro-3H-2,4-benzodioxepine of the formula:

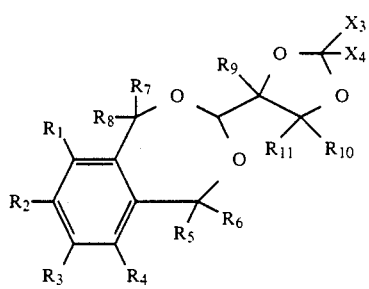

wherein
- $R_1$, $R_2$, $R_3$ or $R_4$ are independently chosen from the group consisting of H, alkyl, aryl, hydroxy, alkoxy, aryloxy, halo, nitro, amino and cyano;
- $R_5$, $R_6$, $R_7$, $R_8$, $R_9$, $R_{10}$ or $R_{11}$ are independently chosen from the group consisting of H, alkyl and aryl; and
- $X_3$ and $X_4$ are independently chosen from the group consisting of H, alkyl and aryl.

4. A substituted 1,5-dihydro-3H-2,4-benzodioxepine of the formula:

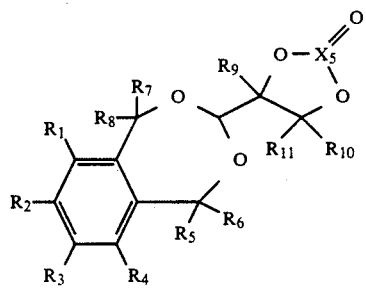

wherein
- $R_1$, $R_2$, $R_3$ or $R_4$ are independently chosen from the group consisting of H, alkyl, aryl, hydroxy, alkoxy, aryloxy, halo, nitro, amino and cyano;
- $R_5$, $R_6$, $R_7$, $R_8$, $R_9$, $R_{10}$ or $R_{11}$ are independently chosen from the group consisting of H, alkyl and aryl; and
- $X_5$ is either C or S.

5. A substituted 1,5-dihydro-3H-2,4-benzodioxepine of the formula:

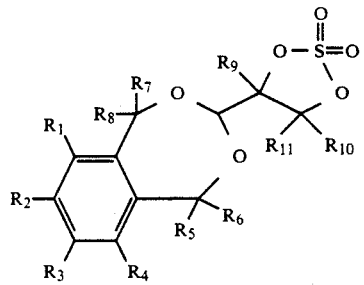

wherein
- $R_1$, $R_2$, $R_3$ or $R_4$ are independently chosen from the group consisting of H, alkyl, aryl, hydroxy, alkoxy, aryloxy, halo, nitro, amino and cyano; and
- $R_5$, $R_6$, $R_7$, $R_8$, $R_9$, $R_{10}$ or $R_{11}$ are independently chosen from the group consisting of H, alkyl and aryl.

6. A substituted 1,5-dihydro-3H-2,4-benzodioxepine of the formula:

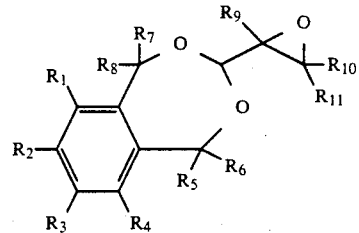

wherein
- $R_1$, $R_2$, $R_3$, or $R_4$ are independently chosen from the group consisting of H, alkyl, aryl, hydroxy, alkoxy, aryloxy, halo, nitro, amino and cyano; and
- $R_5$, $R_6$, $R_7$, $R_8$, $R_9$, $R_{10}$ or $R_{11}$ are independently chosen from the group consisting of H, alkyl and aryl.

7. The composition of claim 6 wherein $R_1$, $R_2$, $R_3$, $R_4$, $R_5$, $R_6$, $R_7$, $R_8$, $R_9$, $R_{10}$ and $R_{11}$ are H.

8. A substituted 1,5-dihydro-3H-2,4-benzodioxepine of the formula:

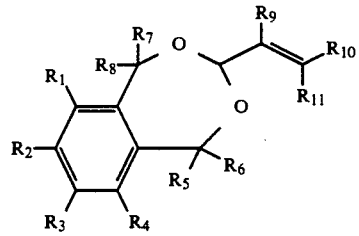

wherein
- $R_1$, $R_2$, $R_3$ or $R_4$ are independently chosen from the group consisting of H, alkyl, aryl, hydroxy, alkoxy, aryloxy, halo, nitro, amino and cyano; and
- $R_5$, $R_6$, $R_7$, $R_8$, $R_9$, $R_{10}$ or $R_{11}$ are independently chosen from the group consisting of H, alkyl and aryl.

* * * * *